(12) United States Patent
Tonner et al.

(10) Patent No.: US 10,842,789 B2
(45) Date of Patent: Nov. 24, 2020

(54) TREATMENT OF SCHIZOPHRENIA

(71) Applicant: PIERRE FABRE MEDICAMENT, Boulogne-Billancourt (FR)

(72) Inventors: Françoise Tonner, Toulouse (FR); Armida Mucci, Naples (IT)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 16/180,641

(22) Filed: Nov. 5, 2018

(65) Prior Publication Data

US 2019/0134026 A1 May 9, 2019

Related U.S. Application Data

(60) Provisional application No. 62/581,249, filed on Nov. 3, 2017.

(51) Int. Cl.
*A61K 31/496* (2006.01)
*A61K 31/352* (2006.01)
*A61K 31/495* (2006.01)
*A61P 25/18* (2006.01)

(52) U.S. Cl.
CPC .......... *A61K 31/496* (2013.01); *A61K 31/495* (2013.01); *A61P 25/18* (2018.01); *A61K 31/352* (2013.01)

(58) Field of Classification Search
CPC ............................ A61K 31/496; A61K 31/352
See application file for complete search history.

(56) References Cited

FOREIGN PATENT DOCUMENTS

WO  WO 91/15513    10/1991
WO  WO 2011/027289  3/2011

OTHER PUBLICATIONS

Maust et al. Handbook of clinical Neurology, 2012, pp. 1-9.*
Leucht et al. Schizophrenia Research, 2005, vol. 79, pp. 231-238.*
I. Bitter et al., "Efficacy of F17464, a new preferential D3 antagonist in a placebo-controlled phase 2 study of patients with an acute exacerbation of schizophrenia," 25th European Congress of Psychiatry, poster EPA17-2823 (2017).
R. L. Clarkson et al., "D3 Receptors Regulate Excitability in a Unique Class of Prefrontal Pyramidal Cells," *Journal of Neuroscience*, 37(24), pp. 5846-5860 (2017).
D. Cussac et al., "Human Dopamine $D_3$ Receptors Mediate Mitogen-Activated Protein Kinase Activation Via a Phosphatidylinositol 3-Kinase and an Atypical Protein Kinase C-Dependent Mechanism," Molecular Pharmacology, 56, pp. 1025-1030 (1999).
D. Cussac et al., "[$^3$H]S33084: a novel, selective and potent radioligand at cloned, human dopamine $D_3$ receptors," *Naunyn-Schmiedeberg's Arch Pharmacol*, 361, pp. 569-572 (2000).
D. R. Kay et al., "The Positive and Negative Syndrome Scale (PANSS) for Schizophrenia," Schizophrenia Bulletin, 13(2), pp. 261-278 (1987).
S. Leucht et al., "Second-generation versus first-generation antipsychotic drugs for schizophrenia: a meta-analysis," Lancet, 373, pp. 31-41 (2009).
J. A. Lieberman et al., "Effectiveness of Antipsychotic Drugs in Patients with Chronic Schizophrenia," The New England Journal of Medicine, 353, pp. 1209-1223 (2005).
L. M. Luttrell et al., "Refining Efficacy: Allosterism and Bias in G Protein-Coupled Receptor Signaling", Methods in Molecular Biology, 756, pp. 3-35 (2011).
J. W. Newcomer, "Second-Generation (Atypical) Antipsychotics and Metabolic Effects a Comprehensive Literature Review," CNS Drugs, 19 (suppl 1), pp. 1-93 (2005).
A. Newman-Tancredi et al., "F15063, a potential antipsychotic with $D_2$/$D_3$antagonist, 5-$HT_{1A}$ agonist and $D_4$ partial agonist properties: (I) in vitro receptor affinity and efficacy profile," *British Journal of Pharmacology*, 151, pp. 237-252 (2007).
J. Rabinowitz et al., "Determinants of Antipsychotic Response in Schizophrenia: Implications for Practice and Future Clinical Trials", *J Clin Psychiatry*, 75(4), pp. 308-316 (2014).
A. Schotte et al., "Risperidone compared with new and reference antipsychotic drugs: in vitro and in vivo receptor binding", *Psychopharmacology*, 124, pp. 57-73 (1996).
J. C. Schwartz et al., "The dopamine D3 receptor and its ligands: Therapeutic implications," *Eur. Neuropsychopharmacol.*, 73 (suppl. 4), S166 (2003).
M. J. Sernyak et al., "Antipsychotic Use in the Treatment of Outpatients With Schizophrenia in the VA from Fiscal Years 1999 to 2006," Psychiatric Services, 59(5), pp. 567-569 (2008).
P. Sokoloff et al., "Novel Dopamine Receptor Subtypes as Targets for Antipsychotic Drugs," Annals New-York Academy of Sciences, 757, pp. 278-292 (1995).
P. Sokoloff et al., "Molecular cloning and characterization of a novel dopamine receptor ($D_3$) as a target for neuroleptics," Nature, 347, pp. 146-151 (1990).
P. Sokoloff et al., "F17464, a Selective Dopamine D3 Antagonist/Serotonin 5-HT1A Partial Agonist, as a Clinical Candidate with Wide Ranging Antipsychotic-like Activity in Models of Dopamine and Glutamate Dysfunctions," Neuropsychopharmacology, 39, S571, W153 (2014).
E. P. Whitlock et al., "An approach to addressing subpopulation considerations in systematic reviews: the experience of reviewers supporting the U.S. Preventive Services Task Force," Systematic Reviews, 6:41, pp. 1-25, CAVDV4 (2017).

* cited by examiner

*Primary Examiner* — Samira J Jean-Louis
(74) *Attorney, Agent, or Firm* — Finnegan, Henderson, Farabow, Garrett & Dunner, L.L.P.

(57) ABSTRACT

The present invention relates to a method of treating schizophrenia in a subject in need thereof, the method comprising administering to the subject a therapeutically effective amount of a selective D3 antagonist, wherein said subject has at least one negative symptom (NS) among the following core negative symptoms in PANSS: Blunted Affect (N1), Emotional Withdrawal (N2), Poor Rapport (N3), Passive withdrawal (N4), and Lack of Spontaneity (N6); with moderate or higher severity. Methods for improving the probability of success and/or the effect of a treatment of schizophrenia in a subject in need thereof are also described.

9 Claims, 1 Drawing Sheet

TREATMENT OF SCHIZOPHRENIA

CROSS-REFERENCES TO RELATED APPLICATIONS

This application claims the benefit of priority to U.S. Provisional Application No. 62/581,249, filed on Nov. 3, 2017, which is incorporated herein by reference in its entirety.

FIELD OF THE INVENTION

The present invention relates to a method of treating schizophrenia in a subject in need thereof, the method comprising administering to the subject a therapeutically effective amount of a selective D3 antagonist, wherein said subject has at least one negative symptom (NS) among the following core negative symptoms in PANSS: Blunted Affect (N1), Emotional Withdrawal (N2), Poor Rapport (N3), Passive withdrawal (N4), and Lack of Spontaneity (N6); with moderate or higher severity, wherein said moderate or higher severity corresponds to a score equal to 4 or higher before beginning of said treatment. Methods for improving the probability of success and/or the effect of a treatment of schizophrenia in a subject in need thereof are also described.

BACKGROUND OF THE INVENTION

Schizophrenia

Schizophrenia is a severe mental disorder that is chronic and can often become disabling. It is defined by the Diagnostic and Statistical Manual of Mental Disorders, Fifth Edition, (DSM-5, 2013) as a mental disorder characterized by abnormalities in one or more of the following five symptomatic domains: delusions, hallucinations (auditory hallucinations are the most common), disorganized thinking and speech, grossly disorganized or abnormal motor behavior (including catatonia), and negative symptoms including affective flattening with diminished emotional expressiveness, avolition, alogia, anhedonia and asociality, which refers to the lack of apparent interest in social communications. The disorder is accompanied by significant social or occupational dysfunction, mainly related to the impairment of cognition with difficulties in memory, executive functions, slow processing speed, attention and concentration, as well as to the severity of negative symptoms.

People with schizophrenia are likely to have additional (comorbid) conditions, including major depression and anxiety disorders; the lifetime occurrence of substance abuse is almost 50%. Social problems, such as long-term unemployment, poverty and homelessness, are common. The average life expectancy of people with schizophrenia is 12 to 15 years less than those without, as a result of increased physical health problems and a high suicide rate (about 10%). Diagnosis is based on behavioral observations and the patient's reported experiences.

The onset of symptoms typically occurs in young adulthood, with a global lifetime prevalence of about 0.3-0.7%. Schizophrenia affects around 24 million people worldwide. It occurs 1.4 times more frequently in males than females and typically appears earlier in men; the peak ages of onset are 20-28 years for males and 26-32 years for females.

Treatments of Schizophrenia

Underlying mechanisms of schizophrenia are poorly understood. Those with a diagnosis of schizophrenia have changes in both brain structures and biochemistry. Particular attention has been paid to the dopamine function in the mesolimbic pathway of the brain.

Patients affected by schizophrenia can be treated with drugs called antipsychotics, also known by the name neuroleptics, which reduce the positive symptoms of schizophrenia. Antipsychotics drugs however fail to significantly improve the negative symptoms and cognitive dysfunction in schizophrenia.

The therapeutic effect of antipsychotics is generally acknowledged as resulting from the blockade of receptors of the neuromediator dopamine in the brain. There are five known sub-types of dopamine receptors, called D1, D2, D3, D4 and D5 (Sokoloff et al. *Annals New-York Academy of Sciences* 1995, 757, 278-292). D2 is also known in 2 isoforms: D2L (Long), the major post synaptic subtype, and D2S (Short).

The first-generation or conventional antipsychotics are preferentially D2 receptor blockers with high affinity. Although these medications produce improvement in the positive symptoms of schizophrenia, they often result in serious adverse effects, including extrapyramidal symptoms (EPS) (Schotte et al., *Psychopharmacology*, 1996, 124, 57-73) which are attributed to the blockade of D2 receptors in the striatal region of the brain. Thus, these medications have been superseded by second-generation or atypical antipsychotics, which are now the mainstay of pharmacotherapy for schizophrenia (Sernyak et al. *Psychiatr Serv.* 2008, 59 (5), 567-569).

These newer agents, which frequently also affect serotoninergic function and/or have a weaker dopamine D2 blocking effect, have demonstrated antipsychotic efficacy and are generally associated with a lower propensity for EPS than conventional antipsychotics (Leucht et al. *Lancet* 2009, 373: 31-41). However, several atypical antipsychotics have been associated with metabolic changes, including weight gain, metabolic syndrome, diabetes, and atherogenic dyslipidemia, that increase cardiovascular risk (Newcomer, *CNS Drugs.* 2005, 19 (suppl 1), 1-93).

The choice of which antipsychotic to use is based on benefits, risks and costs. Whether as a drug class the typical or atypical antipsychotics are better is debatable. Both have equal drop-out and symptom relapse rates when typical antipsychotics are used at low to moderate dosages. There is a good response in 40-50% cases, a partial response in 30-40% cases, and treatment resistance (failure of satisfactory response after successive six-week treatment periods with two of three different antipsychotics) in 20-30% of people. Very high individual variability can be observed in response to antipsychotics in schizophrenia. Factors of this variability remains to be elucidated.

Limitations of treatment with well-established antipsychotics (conventional and atypical antipsychotics) were highlighted in the results from the Clinical Antipsychotic Trials of Intervention Effectiveness (CATIE): 74% of patients discontinued treatment with the initially prescribed agent within 18 months because of lack of efficacy, adverse events, or personal preference (Lieberman et al. *N Engl J Med* 2005, 353, 1209-23).

Improvements in Therapeutical Treatments

Improvements in pharmacological treatments are sought by exploring many different and complementary approaches. Most researches aim at finding new compounds or formulations with improved efficacy and/or safety profile, but there are more and more alternative approaches developed, such as precision medicine focusing on determining the most adapted treatment for a given patient.

The scientific rationale for the research of new compounds is based on the hypothesis of disrupted dopaminergic pathway activity in schizophrenia, which is dual: sub-cortical hyperactivity and cortical hypoactivity. Given this pattern, it seems obvious that the mechanism of action of the currently available antipsychotics, by blocking the dopaminergic D2 receptors in both regions, is not optimal in the treatment of schizophrenia. The D2 receptors are located in both brain regions, therefore, while reducing the dopaminergic hyperactivity in the subcortical areas, they impair the dopaminergic hypoactivity in the prefrontal cortex which may account for the cognitive impairment and negative symptoms. On the other hand, the D3 receptors are mainly present in the sub-cortical regions. One of the D3 receptor actions is a negative control on the activity of the mesocortical dopamine neurons; consequently, blocking the D3 receptor would normalize the cortical dopaminergic functioning. D3 receptors are also found in the cortex (Clarkson et al. *Journal of Neuroscience*, 2017, 37 (24) 5846-5860). Although their function has not been fully characterized yet, blockade of the D3 receptor has been suggested as being necessary for the therapeutic effects of antipsychotics (Schwartz et al. Eur. *Neuropsychopharmacol.* 2003, 73 (suppl. 4), S 166). Hence, pharmacological agents that selectively modulate D3 receptor function are thought to be effective antipsychotics almost free from neurological side-effects (WO1991/015513).

WO2011/027289 discloses the N-(3-{4-[4-(8-oxo-8H-[1,3]dioxolo[4,5-g]chromen-7-yl)-butyl]-piperazin-1-yl}-phenyl)-methanesulfonamide (Example no 21) corresponding to formula 1, also called F17464.

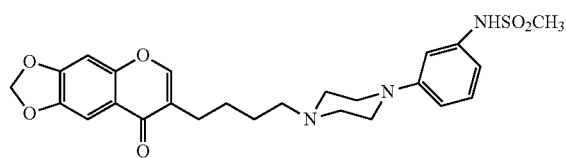

Formula 1

F17464 is a potent, selective dopamine D3 receptor antagonist as well as partial 5HT1A agonist, which makes it unlike any of the currently available medications for schizophrenia.

The activity of F17464 was evaluated at recombinant dopaminergic receptors in vitro for its profile at D2 and D3 receptor. In [$^3$H] spiperone binding studies using cells expressing human recombinant dopamine D3 receptors or human recombinant dopamine D2L or D2S receptors (Cussac et al. *Naunyn-Schmiedeberg's Arch Pharmacol*, 2000, 361, 569-572), the compound behaves as a high affinity dopamine D3 receptor ligand, with Ki value of 0.17 nanomole·liter$^{-1}$. It exhibits a lower affinity for dopamine D2L receptor that is 71 times weaker (Ki value of 12.1 nanomole·liter$^{-1}$) and for dopamine D2S receptor that is 38 times weaker (Ki value of 6.5 nanomole·liter$^{-1}$). F17464 was also evaluated for its agonist, partial agonist, or antagonist activity at the dopamine D3 receptor by using the MAP-kinase activity test on human recombinant dopamine D3 receptors (Cussac et al., *Mol. Pharmacol.* 1999, 56, 1025-1030). Its intrinsic activity was null, indicating that it is a full antagonist.

In pre-clinical studies, it demonstrated antipsychotic-like activity, as well as activity on negative symptoms, and cognitive improvements in several animal models of cognitive deficits. Few side effects were seen in rodent, canine, and also in the initial single and multiple dose studies performed in healthy control subjects.

In a PET-scan clinical study performed in healthy subjects using [11C]-(+)-PHNO, F17464 showed a strong and long-lasting D3 binding rate after two single dose levels, with a modest binding rate to D2 receptor (Sokoloff et al. *Neuropsychopharmacology*, 2014, 39, S571, W153). The efficacy of F17464 has been demonstrated in patients with an acute exacerbation of schizophrenia, in a phase 2 study, with a favorable safety profile (Bitter et al. *25th European congress of psychiatry*, 2017, poster EPA17-2823)

Even if these results are very promising, all problems are not solved and, in particular in the context of schizophrenia, it is still of crucial interest to find an adequate answer to individual variability of response.

Identifying the kind of treatment that would have the most chances to be successful according to the particular profile of the individual patient would have many advantages including reducing patient exposure to ineffective treatments and their side effects, improving adherence to treatment and, overall, enhancing global clinical outcome (Whitlock et al. *Systematic Reviews*, 2017, 6:41).

Several public and/or private research teams work on understanding the factors that determine the response to antipsychotic treatments (for example Rabinowitz et al. *J Clin Psychiatry* 2014, 75 (4), 308-316).

However, as determinants of treatment response are poorly understood, it is very difficult to address the heterogeneity of treatment effects. Thus, there is a real need, in particular in the treatment of schizophrenia, to identify "better responders", which are subpopulations that would benefit more of a given treatment, when compared to the larger population.

BRIEF SUMMARY OF THE INVENTION

Surprisingly, the inventors have detected that a particular population of patients better responds to a treatment with a selective D3 antagonist than the total schizophrenic population.

It has been found out that better treatment results were obtained in a subgroup of patients having at least one negative symptom (NS) among the following core negative symptoms in PANSS (Positive And Negative Symptoms Scale):

Blunted Affect (N1),
Emotional Withdrawal (N2),
Poor Rapport (N3),
Passive withdrawal (N4), and
Lack of Spontaneity (N6), with moderate or higher severity, i.e. corresponding to a score equal to 4 or higher at baseline.

This is illustrated by the example 1, in a phase II clinical study performed with F17464.

These results were compared to the effect on patients meeting similar negative symptoms criteria from the NEW-MEDS database (Rabinowitz et al, *J Clin Psychiatry* 2014; 75 (4):308-316). None of the registered atypical antipsychotics analysed (with PANSS items scores available; none selective D3 antagonists) showed the same kind of results.

Thus, the present invention relates to a method of treating schizophrenia in a subject in need thereof, the method comprising administering to the subject a therapeutically effective amount of a selective D3 antagonist, preferably of F17464 or a pharmaceutically acceptable salt thereof, wherein said subject has at least one negative symptom (NS) among the following core negative symptoms in PANSS:
    Blunted Affect (N1),
    Emotional Withdrawal (N2),
    Poor Rapport (N3),
    Passive withdrawal (N4), and
    Lack of Spontaneity (N6);
with moderate or higher severity, wherein said moderate or higher severity corresponds to a score equal to 4 or higher before beginning of said treatment.

The invention also relates to a method of improving the probability of success and/or the effect of a treatment of schizophrenia in a subject in need thereof comprising administering to the subject a therapeutically effective amount of a selective D3 antagonist, preferably of F17464 or a pharmaceutically acceptable salt thereof, wherein said subject has at least one negative symptom (NS) among the following core negative symptoms in PANSS:
    Blunted Affect (N1),
    Emotional Withdrawal (N2),
    Poor Rapport (N3),
    Passive withdrawal (N4), and
    Lack of Spontaneity (N6),
with moderate or higher severity, wherein said moderate or higher severity corresponds to a score equal to 4 or higher before beginning of said treatment.

In some embodiments, the pharmaceutically acceptable salt according to the invention is F17464 hydrochloride.

In some embodiments, the subject according to the invention suffers from acute exacerbation of schizophrenia before beginning of the treatment according to the invention.

In some preferred embodiments, the acute exacerbation of schizophrenia according to the invention is characterized by a PANSS total score higher or equal to 70 and lower than 120.

In some embodiments, the subject according to the invention meets the following criteria:
    a. well-documented diagnosis of schizophrenia for a minimum of 1 year; and
    b. a Clinical Global Impression of Severity (CGI-S) score≥4
before beginning of said treatment.

In some embodiments, the therapeutically effective amount according to the invention is a dose of 1 to 100 mg daily, preferably 40 mg daily.

In some preferred embodiments, the therapeutically effective amount according to the invention is a dose of 1 to 100 mg once daily or 0.5 to 50 mg twice daily.

In some more preferred embodiments, the therapeutically effective amount according to the invention is a fixed dose of 1 to 100 mg once daily or 0.5 to 50 mg twice daily, preferably 40 mg once daily or 20 mg twice daily.

In some embodiments, the dose according to the invention is administered orally.

In some embodiments, the dose according to the invention is administered for 6 weeks or more to the subject in need thereof.

DETAILED DESCRIPTION OF THE INVENTION

Figure 1:
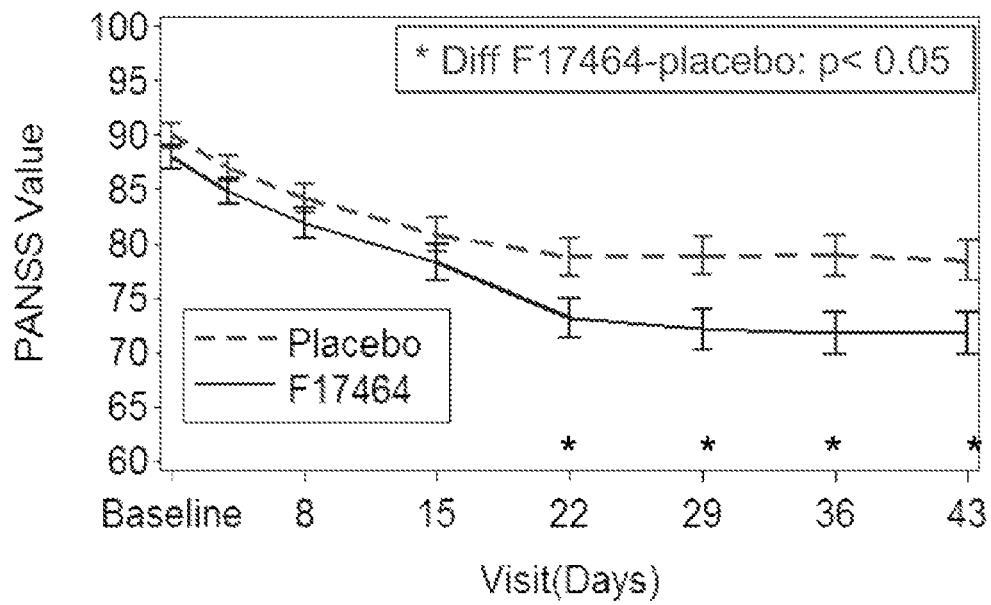
FIG. 1 shows PANSS total score values over time (LOCF) [FAS] (Mean/SEM Standard Error of the Mean) during the F17464 clinical study detailed in example 1.

A novel method of treatment of schizophrenia, comprising administering to a subject in need thereof an effective amount of a selective D3 antagonist, preferably of F17464, wherein said subject has at least one negative symptom (NS) among the following core negative symptoms in PANSS:
    Blunted Affect (N1),
    Emotional Withdrawal (N2),
    Poor Rapport (N3),
    Passive withdrawal (N4), and
    Lack of Spontaneity (N6);
with moderate or higher severity, i.e. corresponding to a score equal to 4 or higher before beginning of said treatment, is provided herein.

The inventors found out that treating with a selective D3 antagonist this particular subpopulation achieved a better response to the treatment. Thus, selecting that subpopulation for a treatment with a selective D3 antagonist improves the probability of success and/or the effect of the treatment.

Definitions

In the context of the present invention, the term "F17464" refers to N-(3-{4-[4-(8-oxo-8H-[1,3]dioxolo[4,5-g]chromen-7-yl)-butyl]piperazin-1-yl}-phenyl)-methanesulfonamide.

The expression "pharmaceutically acceptable" refers to that which is useful in the preparation of a pharmaceutical composition, that is generally safe, nontoxic and neither biologically or otherwise undesirable and that is acceptable for veterinary and human use.

As used here, the term "salts" denotes organic or inorganic acid and base addition salts of a compound, preferably organic or inorganic acid addition salts of a compound. As example, mention may be made of the salts derived from inorganic acids such as hydrochloric, hydrobromic, phosphoric, sulfuric acids, and those derived from organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic acids.

As used above, the term "D3 dopamine receptor", "D3 receptor" or "D3" denotes a dopamine receptor sub-type mainly expressed in the limbic system (Sokoloff et al. *Nature*, 1990, 347, 146-151). The D3 receptor is described in international application WO1991/015513.

In the context of the present invention, the expression "D3 antagonist" refers to a potential D3 receptor blocker, that is to say a molecule that forms a complex with D3 receptor and that stabilizes, totally or partially, the D3 receptor in an inactive state, may it be an antagonist (inverse agonist or neutral antagonist), a partial agonist or a negative allosteric modulator (Luttrell et al. *Methods in Molecular Biology*, 2011, 756, 3-35).

As used herein, the term "selective D3 antagonist" refers to a D3 antagonist, as defined here above, that has more affinity for the D3 receptor than for the D2 receptor (D2S and/or D2L). Affinity of a compound for a receptor is usually expressed as a Ki value. Preferentially, the relative binding affinities are determined in competitive radioligand binding studies using cells expressing human recombinant dopamine D3, D2S or D2L receptors (Newman-Tancredi et al. *British Journal of Pharmacology*, 2007, 151, 237-252). More preferentially, it is defined in [$^3$H] spiperone binding studies using cells expressing human recombinant dopamine D3 receptors or human recombinant dopamine D2L or D2S receptors (Cussac et al. *Naunyn-Schmiedeberg's Arch Pharmacol,* 2000, 361, 569-572).

According to the invention, the terms "subject" or "patient" refers to a human or non-human mammal affected or very susceptible to being affected by a pathology. Preferably, the patient is a human.

As used herein, the terms "therapeutically active amount" means an amount of a compound or a composition that is effective in obtaining the desired therapeutic effect when administered to a subject.

The terms "treating" or "treatment" are used herein, unless otherwise indicated, to mean to relieve, alleviate, delay, reduce, reverse, improve, or prevent at least one symptom of a disease, disorder or condition. They may also mean to stop, delay the onset and/or reduce the risk of developing or worsening of at least one symptom of a disease, disorder or condition. "Schizophrenia" is defined herein according to the Diagnostic and Statistical Manual of Mental Disorders, Fourth-Revised (DSM-4-TR).

Acute exacerbation of schizophrenia is often associated with the presence of florid psychotic features (acute psychotic episode), marked by characteristic positive symptoms of hallucinations, delusions, conceptual disorganization, behavioral disturbances and excitement. Other non-specific indicators such as suicidal behaviour can also be taken into account. The decision to hospitalize refers to multiple factors such as mood disorder, suicide attempts, drug abuse or social and environmental problems, the patient's being considered to pose a serious threat of harm to self or others, being unable to care for self, needing constant supervision and general medical or psychiatric problems that make outpatient treatment unsafe or ineffective. In the context of the present invention, "acute exacerbation of schizophrenia" is a sudden worsening of the symptoms of schizophrenia that may require the hospitalization of the patient.

As used herein, "well-documented diagnosis" means that a full history of the patient is recorded in his/her medical file, which is available and provides a reliable description of the events and symptoms that are supporting the diagnostic criteria.

The abbreviation "PANSS" stands for Positive And Negative Syndrome Scale as defined in Kay et al. *Schizophrenia Bulletin,* 1987, 13, 2, 261-78. This scale is composed of 30 items that are evaluated on 7-point rating scores (1: Absent, 2: Minimal, 3: Mild, 4: Moderate, 5: Moderate to severe, 6: severe, 7: Extreme). Among the 30 items, 7 constitute the Positive Symptoms sub-scale, 7 constitute the Negative Symptoms sub-scale, and the remaining 16 the General Psychopathology sub-scale.

The expressions "response to" or "effect of" or "efficacy of" a treatment is defined as a quantitative assessment of the impact of the treatment using recommended efficacy measure(s) and/or evaluation(s) according to the pathology. Preferably, in the context of the present invention, the efficacy of a treatment of schizophrenia is defined by its effect in reducing the PANSS total and/or sub-scores between beginning and end of the treatment.

DETAILED DESCRIPTION

The present invention concerns a method of treating schizophrenia in a subject in need thereof, the method comprising administering to the subject a therapeutically effective amount of a selective D3 antagonist, wherein said subject has at least one negative symptom (NS) among the following core negative symptoms in PANSS (Positive and Negative Syndrome Scale):

Blunted Affect (N1),
Emotional Withdrawal (N2),
Poor Rapport (N3),
Passive withdrawal (N4), and
Lack of Spontaneity (N6), with moderate or higher severity, wherein said moderate or higher severity corresponds to a score equal to 4 or higher before beginning of said treatment.

The present invention also concerns a method of improving the probability of success and/or the effect of a treatment of schizophrenia in a subject in need thereof, the method comprising administering to the subject a therapeutically effective amount of a selective D3 antagonist, wherein said subject has at least one negative symptom (NS) among the following core negative symptoms in PANSS:

Blunted Affect (N1),
Emotional Withdrawal (N2),
Poor Rapport (N3),
Passive withdrawal (N4), and
Lack of Spontaneity (N6), with moderate or higher severity, wherein said moderate or higher severity corresponds to a score equal to 4 or higher before beginning of said treatment.

The present invention thus also concerns a selective D3 antagonist for use in the treatment of schizophrenia in a subject in need thereof, characterized in that it comprises administering to the subject a therapeutically effective amount of said selective D3 antagonist, wherein said subject has at least one negative symptom (NS) among the following core negative symptoms in PANSS (Positive and Negative Syndrome Scale):

Blunted Affect (N1),
Emotional Withdrawal (N2),
Poor Rapport (N3),
Passive withdrawal (N4), and
Lack of Spontaneity (N6), with moderate or higher severity, wherein said moderate or higher severity corresponds to a score equal to 4 or higher before beginning of said treatment.

In some preferred embodiments, said selective D3 antagonist for use according to the invention, is for improving the probability of success and/or the effect of the treatment of schizophrenia.

The present invention also relates to the use of a selective D3 antagonist for the manufacture of a medicine for the treatment of schizophrenia in a subject in need thereof, characterized in that it comprises administering to the subject a therapeutically effective amount of said selective D3 antagonist, wherein said subject has at least one negative symptom (NS) among the following core negative symptoms in PANSS (Positive and Negative Syndrome Scale):

Blunted Affect (N1),
Emotional Withdrawal (N2),
Poor Rapport (N3),
Passive withdrawal (N4), and
Lack of Spontaneity (N6), with moderate or higher severity, wherein said moderate or higher severity corresponds to a score equal to 4 or higher before beginning of said treatment.

The present invention also concerns the use of a selective D3 antagonist for the manufacture of a medicine for improving the probability of success and/or the effect of the treatment of schizophrenia in a subject in need thereof, characterized in that it comprises administering to the subject a therapeutically effective amount of said selective D3 antagonist, wherein said subject has at least one negative symptom (NS) among the following core negative symptoms in PANSS (Positive and Negative Syndrome Scale):
  Blunted Affect (N1),
  Emotional Withdrawal (N2),
  Poor Rapport (N3),
  Passive withdrawal (N4), and
  Lack of Spontaneity (N6),
with moderate or higher severity, wherein said moderate or higher severity corresponds to a score equal to 4 or higher before beginning of said treatment.

Selective D3 Antagonists

In the context of the present invention, a "selective D3 antagonist" is a compound that has more affinity for the D3 receptor than for the D2 receptor (D2S and/or D2L).

In some embodiments, the selective D3 antagonist according to the invention has a Ki ratio D2/D3>1, preferably ≥2, preferably ≥5, preferably ≥10, preferably ≥20, preferably ≥30, preferably ≥40, preferably ≥50, preferably ≥60, preferably ≥70.

In some embodiments, the selective D3 antagonist according to the invention is N-(3-{4-[4-(8-oxo-8H-[1,3]dioxolo[4,5-g]chromen-7-yl)-butyl]-piperazin-1-yl}-phenyl)-methanesulfonamide of the following formula 1, also called F17464, or a pharmaceutically acceptable salt thereof.

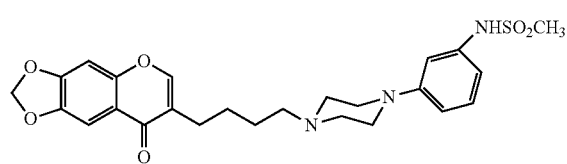

Formula 1

In some preferred embodiments, the pharmaceutically acceptable salt according to the invention is N-(3-{4-[4-(8-oxo-8H-[1,3]dioxolo[4,5-g]chromen-7-yl)-butyl]-piperazin-1-yl}-phenyl)-methanesulfonamide hydrochloride.

Subjects

The subject according to the invention has at least one negative symptom (NS) among the following core negative symptoms in PANSS (Positive and Negative Syndrome Scale):
  Blunted Affect (N1),
  Emotional Withdrawal (N2),
  Poor Rapport (N3),
  Passive withdrawal (N4), and
  Lack of Spontaneity (N6),
with moderate or higher severity, wherein said moderate or higher severity corresponds to a score equal to 4 or higher before beginning of the treatment according to the invention.

In some embodiments, the subject according to the invention is 18 or more than 18 years old.

In some embodiments, the subject according to the invention is 64 or less than 64 years old.

In some preferred embodiments, the subject according to the invention is between 18 and 64 years old or 18 or 64 years old.

In some embodiments, the subject has a diagnosis of schizophrenia.

In some preferred embodiments, the subject has a diagnosis of schizophrenia for a minimum of 1 year before beginning of the treatment according to the invention.

In some more preferred embodiments, the subject has a well-documented diagnosis of schizophrenia for a minimum of 1 year before beginning of the treatment according to the invention.

In some preferred embodiments, the well-documented diagnosis according to the invention includes the description of a hospitalization for acute exacerbation of schizophrenia, more particularly the first hospitalization for acute exacerbation of schizophrenia.

In some embodiments, the subject according to the invention has a number of hospitalizations not higher than 2 per year between diagnosis and beginning of the treatment according to the invention.

In some embodiments, the subject according to the invention has a number of hospitalizations of at least 1 and not higher than 2 per year between diagnosis and beginning of the treatment according to the invention.

In some preferred embodiments, the hospitalization according to the invention has a minimum duration of hospitalization of more than 4 days.

In some embodiments, the subject according to the invention had maximum 3 acute psychotic episodes that required hospitalization or change of antipsychotic medication or other therapeutic intervention during the year before beginning of the treatment according to the invention.

In some embodiments, the subject according to the invention suffers from acute exacerbation of schizophrenia before beginning of the treatment according to the invention.

In some embodiments, the acute exacerbation according to the invention is characterized by a PANSS total score higher or equal to 70 and lower than 120.

In some embodiments, the acute exacerbation according to the invention is characterized by a rating of at least 4 (moderate) on at least 2 of the following 4 PANSS positive symptoms: delusions, hallucinatory behavior, conceptual disorganization, suspiciousness/persecution.

In some embodiments, the acute exacerbation according to the invention is not associated with clinically predominant negative symptoms.

As used herein, "clinically predominant negative symptoms" means that the predominance of the negative symptoms is not pre-defined with objective criteria such as a PANSS negative score threshold but is assessed by the clinician based on his clinical judgement.

In some embodiments, the acute exacerbation according to the invention is characterized by a Clinical Global Impression of Severity (CGI-S) score ≥4 (moderate or severe).

In some embodiments, the acute exacerbation according to the invention is not the first acute episode of exacerbation of the subject according to the invention.

In some embodiments, the subject according to the invention does not suffer from one or several of the following:
  Schizoaffective disorder, schizophreniform disorder and other psychotic disorders;
  Bipolar I and II disorder;
  Pervasive developmental disorder, mental retardation, delirium, dementia, memory impairment and other cognitive disorders that would compromise a reliable diagnosis according to the invention;
  History of tardive dyskinesia or chronic extra-pyramidal symptoms (EPS), serotonin syndrome or neuroleptic malignant syndrome;
  Major depressive disorder which requires a pharmacological treatment;
  At imminent risk of injuring him/herself or others or causing significant damage to property;

Suicidal risk based on the Columbia-Suicide Severity Rating Scale (CSSRS):
Any suicidal behavior in the past year,
Suicidal ideation of type 4 or 5 in the past month,
Lack of significant improvement (no significant relief of symptoms, and no period of good function) despite adequate courses with at least 3 different antipsychotics medication cycles of an adequate duration (at least 4 weeks) and at adequate dosage during the previous 5 years;
before beginning of the treatment according to the invention.

In some embodiments, the subject according to the invention meets one or several of the eligibility criteria described in example 1 paragraph 2.2.

In some embodiments, the subject according to the invention does not meet one or several of the non-eligibility criteria described in example 1 paragraph 2.3.

In some preferred embodiments, the subject according to the invention meets one or several of the eligibility criteria described in example 1 paragraph 2.2 and does not meet one or several of the non-eligibility criteria described in example 1 paragraph 2.3.

In some preferred embodiments, the subject according to the invention meets all the eligibility criteria described in example 1 paragraph 2.2 and does not meet any of the non-eligibility criteria described in example 1 paragraph 2.3.

In some preferred embodiments, the subject according to the invention suffers from acute exacerbation of schizophrenia and meets the following criteria:
a. a well-documented diagnosis of schizophrenia for a minimum of 1 year;
b. a PANSS total score higher or equal to 70 and lower than 120; and
c. a Clinical Global Impression of Severity (CGI-S) score ≥4
before beginning of the treatment according to the invention.

Treatment of Schizophrenia

Preferably, the effect of a treatment of schizophrenia according to the invention is assessed by the reduction in the PANSS total and/or at least one sub-score between beginning and end of the treatment.

In some embodiments, the improvement of the effect according to the invention is a ≥50% additional reduction in the PANSS total and/or any sub-score between beginning and end of the treatment, as compared to the average effect of the same treatment according to the invention performed on subjects who meet all the characteristics of the subject according to the invention as detailed in the present description except that they have negative symptom (NS) among the following core negative symptoms in PANSS (Positive and Negative Syndrome Scale):
Blunted Affect (N1),
Emotional Withdrawal (N2),
Poor Rapport (N3),
Passive withdrawal (N4), and
Lack of Spontaneity (N6),
with any severity, wherein said any severity corresponds to a score equal to 1 or higher before beginning of the treatment according to the invention.

In some preferred embodiments, the improvement of the effect according to the invention is a ≥50% additional reduction in the PANSS total and all sub-scores between beginning and end of the treatment.

In some embodiments, the improvement of the effect according to the invention is a ≥100% additional reduction in the PANSS total and/or any sub-score between beginning and end of the treatment.

In the context of the present invention, the term "success of a treatment" refers to a significant reduction of 20% or more of the PANSS total and/or any sub-score between beginning and end of the treatment.

In some embodiment, the success according to the invention is a significant reduction of 20% or more of the PANSS total score between beginning and end of the treatment.

In some preferred embodiment, the success according to the invention is a significant reduction of 30% or more of the PANSS total and/or any sub-score between beginning and end of the treatment.

In some preferred embodiment, the success according to the invention is a significant reduction of 30% or more of the PANSS total score between beginning and end of the treatment.

In some more preferred embodiment, the success according to the invention is a significant reduction of 40% or more of the PANSS total and/or any sub-score between beginning and end of the treatment.

In some more embodiment, the success according to the invention is a significant reduction of 40% or more of the PANSS total score between beginning and end of the treatment.

The term "probability of success", as used herein, refers to the percentage of subjects wherein the treatment is a success according to the invention.

In some embodiments, the improvement of the probability of success according to the invention is ≥5% additional subjects wherein the treatment is a success according to the invention, as compared to the probability of success of the same treatment according to the invention performed on subjects who meet all the characteristics of the subjects according to the invention as detailed in the present description except that they have negative symptom (NS) among the following core negative symptoms in PANSS (Positive and Negative Syndrome Scale):
Blunted Affect (N1),
Emotional Withdrawal (N2),
Poor Rapport (N3),
Passive withdrawal (N4), and
Lack of Spontaneity (N6),
with any severity, wherein said any severity corresponds to a score equal to 1 or higher before beginning of the treatment according to the invention.

In some preferred embodiments, the improvement of the probability of success according to the invention is ≥10% additional subjects wherein the treatment is a success according to the invention.

In some more preferred embodiments, the improvement of the probability of success according to the invention is ≥15% additional subjects wherein the treatment is a success according to the invention.

Dosing & Treatment Regimen

The specific dose level and regimen of the selective D3 antagonist to be administered according to the invention, for any particular patient, will depend on a variety of factors, including body weight, general health, sex, diet, duration, method and route of administration, levels of intestinal absorption and resorption and of excretion, combination with other medicaments and the severity of the particular condition being treated, any history of response to previous antipsychotic treatments, and history of particular adverse events reported with previous antipsychotic treatments.

In some embodiments, the therapeutically effective amount according to the invention is a dose of 1 to 100 mg daily, preferably 40 mg daily.

In some preferred embodiments, the therapeutically effective amount according to the invention is a dose of 1 to 100 mg once daily or 0.5 to 50 mg twice daily.

In some preferred embodiments, the therapeutically effective amount according to the invention is a fixed dose.

In some more preferred embodiments, the therapeutically effective amount according to the invention is a fixed dose of 1 to 100 mg once daily or 0.5 to 50 mg twice daily, preferably 40 mg once daily or 20 mg twice daily.

It may be necessary to use doses and regimen outside these ranges and schemes as determined by the person skilled in the art.

The therapeutically effective amount according to the present invention may be administered to a subject by various routes, e.g. orally, transdermally, perineurally or parenterally, among others, including nasal or rectal routes. It will be appreciated that the preferred route will depend on the general condition and age of the subject.

In some preferred embodiments, the dose according to the invention is administered orally.

The duration of the treatment according to the invention will also depend on a variety of factors.

In some embodiments, the dose according to the invention is administered for 6 weeks or at least 6 weeks to the subject in need thereof.

Although the foregoing invention has been described in some detail by way of illustration and example for purposes of clarity of understanding, it will be readily apparent to those ordinary skill in the art in light of the teachings of this invention that certain changes and modifications may be made thereto without departing from the spirit or scope of the appended claims.

The following examples are merely illustrative of the present invention and should not be construed as limiting the scope of the invention in any way.

EXAMPLES

Example 1: Analysis of F17464 Clinical Study Results

N-(3-{4-[4-(8-oxo-8H-[1,3]dioxolo[4,5-g]chromen-7-yl)-butyl]-piperazin-1-yl}-phenyl)-methanesulfonamide hydrochloride has been tested in a placebo-controlled study of patients with an acute exacerbation of schizophrenia.

2.1 Methods

This double-blind, parallel group, multicenter study included patients with acute exacerbation of schizophrenia treated either with F17464 fixed dose 40 mg (20 mg bid) or placebo (randomization 1:1) for 6 weeks as antipsychotic monotherapy. The primary objective was to evaluate the efficacy of F17464 in comparison to placebo. The primary efficacy criterion was the PANSS (Positive and Negative Syndrome Scale) total score change from baseline to Day 43 on the Full Analysis Set (FAS).

Inclusion criteria included a well-documented diagnosis of schizophrenia for a minimum of 1 year, and a recent acute exacerbation characterized by a PANSS total score at screening ≥70 and <120 with no significant change of the PANSS positive subscore between the screening and randomization visits; and Clinical Global Impression of Severity (CGI-S) score ≥4.

All patients had discontinued previous treatments within the week prior to administration of study medication.

Following screening, patients were maintained in hospital till the 3rd week of treatment. Patients who had CGI-I (Clinical Global Impression of Improvement) score of ≤3 after 3 or 4 weeks were then eligible for hospital discharge and could continue study participation as outpatients.

The PANSS scores of the tested patients were established each week.

2.2 Detailed Eligibility Criteria

Demographic and Other Characteristics:
  Male or female, 18-64 years of age inclusive
Diagnostic Criteria:
  Schizophrenia History: Before Screening Visit
    Patient with a current primary diagnosis of schizophrenia undergoing an acute exacerbation with prominent "active phase" symptoms, as described by the Diagnostic and Statistical Manual of Mental Disorders, 4th edition—Text Revision (DSM IV-TR) using the MINI 6.0 (Mini-International Neuropsychiatric Interview) for schizophrenia and psychotic disorders related to DSM IV-TR;
    For a minimum of 1 year, well-documented diagnosis with the first hospitalization for acute exacerbation of schizophrenia;
    Since the diagnosis of schizophrenia, the average number of hospitalizations should be no higher than 2 per year (the minimum duration of hospitalization should be more than 4 days);
    During the year before screening visit, maximum 3 acute psychotic episodes that required hospitalization or change of antipsychotic medication or other therapeutic intervention;
    Adequate clinical response to well-conducted treatment courses during previous acute episodes. A well conducted treatment course is defined as an antipsychotic treatment with the usual doses for at least 4 weeks.
  Current Acute Episode:
    Structured Clinical Interview for the Positive And Negative Syndrome Scale (SCI-PANSS) with a PANSS total score ≥70 to <120 (at screening and randomization visits);
    Rating of at least 4 (moderate) on at least 2 of the following 4 PANSS positive symptoms: delusions, hallucinatory behavior, conceptual disorganization, suspiciousness/persecution;
    Clinical Global Impression of Severity (CGI-S) score ≥4 (moderate or severe).
    Antipsychotic initiated for this acute episode and/or ongoing chronic antipsychotic treatment, with a maximum of 2 antipsychotics in total needed to be changed (due to inefficacy or safety reasons);
    Hospitalization and/or treatment for the current psychotic episode for less than 2 weeks prior to screening visit;
    No significant improvement of PANSS total score between enrolment (screening visit) and inclusion (randomization visit) corresponding to a score improvement <20% on positive symptoms subscale.
Examination:
  Normal physical examination results, vital signs and clinical laboratory test results or other results judged not clinically significant by the investigator;
  Body mass index (BMI)≥18 and ≤35 kg/m$^2$ inclusive.

Ethical/Legal Considerations:
  Patient able to read and understand the information leaflet and to give his/her written informed consent before the initiation of any study specific procedures;
  Patient able to accept all the constraints of the study in the investigator's opinion, in particular with regard to the duration of the hospitalization in the clinical center and compliance to treatment after discharge;
  Patient able to report all intercurrent events that might occur during the study.

2.3 Non-Eligibility Criteria

Related to the Pathology:
  Patients in their first acute episode of psychosis;
  Current schizophrenic episode with predominant negative symptoms;
  Patient «known to be refractory» defined as lack of significant improvement (no significant relief of symptoms, and no period of good function) despite adequate courses with at least 3 different antipsychotics medication cycles of an adequate duration (at least 4 weeks) and at adequate dosage during the previous 5 years;
  Schizoaffective disorder, schizophreniform disorder and other psychotic disorders;
  Bipolar I and II disorder;
  Pervasive developmental disorder, mental retardation, delirium, dementia, memory impairment and other cognitive disorders that would compromise a reliable assessment according to the investigator's opinion;
  Known or suspected borderline or antisocial personality disorder or other DSM IV-TR axis II disorder of sufficient severity to interfere with participation in this study;
  History of tardive dyskinesia or chronic extra-pyramidal symptoms (EPS), serotonin syndrome or neuroleptic malignant syndrome;
  Major depressive disorder which requires a pharmacological treatment;
  At imminent risk of injuring him/herself or others or causing significant damage to property, as judged by the investigator;
  Suicidal risk based on the Columbia-Suicide Severity Rating Scale (CSSRS):
    Any suicidal behavior in the past year,
    Suicidal ideation of type 4 or 5 in the past month.
Related to Treatments:
  Structured psychotherapy (e.g. cognitive behavioral therapy) started within 6 weeks before screening visit;
  Electroconvulsive therapy within 3 months before screening visit;
  Previous lack of response to electroconvulsive therapy;
  Treatment ongoing with a depot neuroleptic (even if less than 1 cycle in duration before screening visit);
  Patient having previous treatment course with clozapine within 4 months prior to screening visit;
  Requirement of concomitant treatment with any of the prohibited medications, supplements, herbal products or products listed in "Prohibited concomitant treatments for associated drug-drug interactions", including any psychotropic drug or any drug with psychotropic activity or with a potentially psychotropic component;
  History of intolerance or hypersensitivity to other drugs of the same chemical class as F17464 or to rescue medications or any history of severe drug allergy or hypersensitivity.

Related to Medical Conditions:
  History or presence of any significant or uncontrolled medical finding such as cancer or neurological, cardiac, hepatic, metabolic, renal, haematological, muscular, endocrine, respiratory, gastrointestinal, dermatological, venereal disorders or diseases, or of any other significant medical condition that may impact the safety, the interpretation of the results, that might affect the absorption, distribution, biotransformation or excretion of the investigational product and/or the participation of the patient in the study according to the opinion of the investigator;
  History of seizure disorder, stroke, significant head injury, severe chronic movement disorder or psychiatric symptoms possibly secondary to any other organic medical condition;
  Known human immunodeficiency virus (HIV) or hepatitis B or C infection;
  Liver enzyme tests (AST, ALT)>2× upper limit of normal or any abnormal level judged as clinically significant by the investigator;
  ECG out of normal ranges (45≤Heart Rate≤90 bpm, 120≤PR≤200 ms, QRS≤110 ms, QTcF≤450 ms for males and ≤470 for female patients) and judged as clinically significant by the investigator;
  For women, pregnancy or in post-partum period or a nursing mother.
Related to Habits:
  Substance or alcohol abuse within the prior 6 months or dependence (other than benzodiazepines, nicotine or caffeine) assessed using the MINI 6.0 for schizophrenia and psychotic disorders related to DSM IV-TR;
  Positive result from the Urine Drug Screen (UDS).
Others:
  The patient is a family member or work associate of one member of the investigational site personnel;
  Is in a position likely to represent a conflict of interest;
  Has participated in a previous F17464 study;
  Has participated in another clinical trial within the last 6 months, has received treatment with known remnant effects or undergone investigation liable to interfere with the present clinical trial;
  Is participating in another clinical trial;
  Patient having forfeited his/her freedom by an administrative or legal obligation or being under guardianship;
  Is mentally unable to understand the nature, objectives and possible consequences of the trial; or refusing to subject himself/herself to its constraints.

2.4 Results on the FAS Population

A total of 134 patients were randomized to placebo or F17464 (67 patients in each group).

As illustrated in Table 1 below, fifty-three patients (39.6%) discontinued the study treatment prematurely (34.3% in the F17464 group and 44.8% in the placebo group). In both groups, the major reasons for premature treatment discontinuation were lack of efficacy or worsening of schizophrenia.

TABLE 1

Patients disposition

| | Placebo (n = 67) | F17464 (n = 67) | Total (n = 134) |
|---|---|---|---|
| Full Analysis Set (FAS) | 67 (100.0%) | 67 (100.0%) | 134 (100.0%) |
| Premature study drug discontinuation | 30 (44.8%) | 23 (34.3%) | 53 (39.6%) |
| Adverse Event | 3 (4.5%) | 2 (3.0%) | 5 (3.7%) |
| Lack Of Efficacy/ Worsening of schizophrenia | 20 (29.9%) | 11 (16.4%) | 31 (23.1%) |
| Withdrawal on Subject decision | 7 (10.4%) | 9 (13.4%) | 16 (11.9%) |
| Other | 0 | 1 (1.5%) | 1 (0.7%) |

All demographic characteristics were comparable between the 2 groups of patients. Baseline PANSS total scores (mean Standard Deviation [SD]) were 90.0 (9.2) in the placebo and 87.9 (9.0) in F17464 group (overall: 88.9 [9.1]), and the sub-scores were similar between treatment groups.

Efficacy:

The primary analysis, on the change from baseline of PANSS total score to Day 43 on the FAS (Last Observation Carried Forward LOCF), showed a statistically significant difference in favor of F17464 over placebo: the adjusted mean Standard Error (SE) change was −14.7 (1.9) on F17464 and −8.5 (2.0) on placebo with a statistically significant treatment effect estimate of −6.2 (2.5). Similar results were obtained on the per protocol set.

From Day 22, the reduction of PANSS total score in the F17464 group was statistically higher than in placebo group as illustrated on FIG. 1.

Secondary criteria analysis supported the primary analysis results:

Effect on positive symptoms: PANSS positive score and positive factor, defined by Marder, were statistically significantly greater in the F17464 group than in the placebo group.

Response rate (RR): PANSS total score reduction from baseline to end of treatment in the F17464 and the placebo groups by:
- 20% RR: 49.3% and 32.8% respectively (p=0.01)
- 30% RR: 27.0% and 15.0% respectively (p=0.04)

Figure 2:
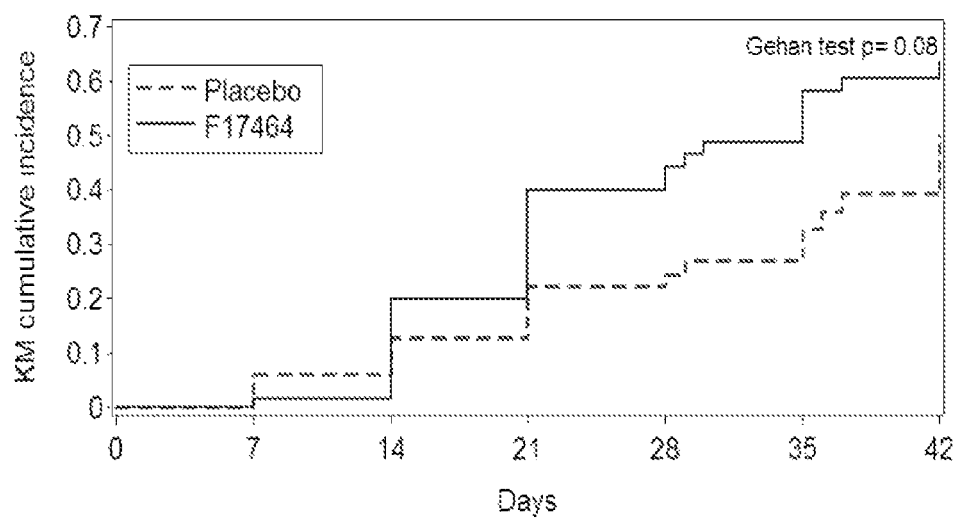
FIG. 2 shows Time to first sustained PANSS 20% response (LOCF)—KM Kaplan-Meyer [FAS] during the F17464 clinical study detailed in example 1.

Time to first sustained PANSS 20% or 30% response: Shorter in F17464 group compared to placebo group from D21 up to Day 42 as illustrated on FIG. 2

Safety:

The overall incidence of treatment-emergent adverse events (TEAEs) was slightly higher in F17464 group (70.1%) than in the placebo group (61.2%). There was no clinically relevant hepatic, metabolic (including clinically relevant weight gain) or cardio-vascular disorder.

2.5 Results on the NS Subgroup

A post-hoc analysis has been performed selecting patients having at least one negative symptom (NS) among the following core negative symptoms in PANSS, named NS subgroup:
- Blunted Affect (N1),
- Emotional Withdrawal (N2),
- Poor Rapport (N3),
- Passive withdrawal (N4), and
- Lack of Spontaneity (N6), with moderate or higher severity, i.e. corresponding to a score equal to 4 or higher at baseline (NS subgroup).

This is illustrated by Table 2 below reporting the results obtained at the end of the study (Day 43).

TABLE 2

Comparison of baseline and changes in PANSS scores in FAS population and NS subgroup according to the invention with at least one negative symptom as defined above

| | FAS population | | NS subgroup | |
|---|---|---|---|---|
| Baseline scores [mean (SD)] | Placebo (n = 67) | F17464 (n = 67) | Placebo (n = 28) | F17464 (n = 29) |
| PANSS total score | 90.0 (9.2) | 87.9 (9.0) | 93.6 (7.9) | 88.8 (9.3) |
| PANSS positive symptoms | 25.2 (3.9) | 24.5 (3.8) | 25.1 (3.4) | 23.3 (3.7) |
| PANSS negative symptoms | 20.3 (3.6) | 19.9 (3.4) | 22.8 (2.9) | 21.9 (3.63) |
| PANSS general psychopathology | 44.4 (5.6) | 43.5 (5.8) | 45.7 (5.2) | 43.6 (6.2) |

| Change from baseline [LSmean (SE)] (a) | FAS population | | NS subgroup | | |
|---|---|---|---|---|---|
| | Placebo (n = 67) | F17464 (n = 67) | Placebo (n = 28) | F17464 (n = 29) | p value |
| PANSS total score[a] | −8.5 (2.0) | −14.7 (1.9) * | −8.9 (3.3) | −21.8 (2.9) * | 0.002 |
| PANSS positive symptoms | −4.5 (0.8) | −6.3 (0.8) * | −4.1 (1.3) | −8.4 (1.2) * | 0.011 |
| PANSS negative symptoms | −1.0 (0.5) | −1.7 (0.4) | −1.6 (0.9) | −4.3 (0.8) * | 0.018 |
| PANSS general psychopathology[a] | −3.0 (1.0) | −6.6 (1.0) * | −2.9 (1.6) | −9.3 (1.5) * | 0.002 |

[LSmean (SE)]: [Least-Square mean (Standard Error)]
(a) adjusted change from baseline;
* statistically significant difference between F17464 and placebo Both populations showed homogenous distribution between treatments (Placebo or F17464) and scores at baseline (PANSS total, PANSS positive symptoms, PANSS negative symptoms and PANSS general psychopathology). PANSS positive symptoms score at baseline was identical in the FAS population compared to NS subgroup, while PANSS negative symptoms score was higher in the NS subgroup compared to FAS population.

The NS subgroup represents 57 patients among the 134 patients of the FAS population (42.5%, 28 patients in the placebo group and 29 in F17464 group.

At day 43, patients treated with placebo in both populations showed globally the same evolution, whereas the patients treated by F17464 showed for the NS subgroup a significantly higher improvement of all their PANSS scores, as illustrated in table 3.

TABLE 3

Comparison of treatment effect on change from baseline PANSS scores in FAS population and subgroup according to the invention with at least one negative symptom as defined above

| Treatment effect on change from baseline [LSmean (SE)] (a) | FAS population F17464 (n = 67) | NS subgroup F17464 (n = 29) | Difference |
|---|---|---|---|
| PANSS total score | −6.2 (2.5) * | −13 (4.1) * | 6.8 (110%) |
| PANSS positive symptoms | −1.9 (1.0) * | −4.3 (1.6) * | 2.4 (126%) |
| PANSS negative symptoms | −0.7 (0.6) | −2.7 (1.1) * | 2 (285%) |
| PANSS general psychopathology | −3.6 (1.3) * | −6.4 (2.0) * | 2.8 (78%) |

(a) adjusted change from baseline
* statistically significant difference between F17464 and placebo These results were compared to the effect on patients meeting similar negative symptoms criteria from the NEW-MEDS database (Rabinowitz et al, *J Clin Psychiatry*, 2014, 75 (4), 308-316). None of the registered atypical antipsychotics represented (with PANSS items scores available) showed the same kind of results.

REFERENCES CITED

Foreign Patent Documents

WO1991/015513
WO2011/027289

OTHER PUBLICATIONS

Diagnostic and Statistical Manual of Mental Disorders, Fourth Edition, (DSM-4 TR, Text Revision)
Diagnostic and Statistical Manual of Mental Disorders, Fifth Edition, (DSM-5) Mini-International Neuropsychiatric Interview, MINI 6.0
Bitter et al. 25*th European congress of psychiatry*, 2017, poster EPA17-2823
Clarkson et al. *Journal of Neuroscience*, 2017, 37 (24) 5846-5860
Cussac et al., *Mol. Pharmacol.* 1999, 56, 1025-1030
Cussac et al. *Naunyn-Schmiedeberg's Arch Pharmacol*, 2000, 361, 569-572
Kay et al. *Schizophrenia Bulletin*, 1987, 13, 2, 261-78
Leucht et al. *Lancet* 2009, 373: 31-41
Lieberman et al. *N Engl J Med* 2005, 353, 1209-23
Luttrell et al. *Methods in Molecular Biology*, 2011, 756, 3-35
Newcomer, *CNS Drugs*. 2005, 19 (suppl 1), 1-93
Newman-Tancredi et al. *British Journal of Pharmacology*, 2007, 151, 237-252
Rabinowitz et al. *J Clin Psychiatry* 2014, 75 (4), 308-316
Schotte et al. *Psychopharmacology*, 1996, 124, 57-73
Schwartz et al. *Eur. Neuropsychopharmacol.* 2003, 73 (suppl. 4), S 166
Sernyak et al. *Psychiatr Serv.* 2008, 59 (5), 567-569
Sokoloff et al. *Annals New-York Academy of Sciences* 1995, 757, 278-292
Sokoloff et al. *Nature,* 1990, 347, 146-151
Sokoloff et al. *Neuropsychopharmacology,* 2014, 39, S571, W153
Whitlock et al. *Systematic Reviews,* 2017, 6:41

The invention claimed is:

1. A method of relieving, alleviating, reversing, or improving at least one symptom of schizophrenia in a subject in need thereof, the method comprising:
    selecting a subject in need of treatment for schizophrenia, wherein the subject has been determined to have at least one negative symptom (NS) among the following core negative symptoms in PANSS (Positive and Negative Syndrome Scale):
        Blunted Affect (N1),
        Emotional Withdrawal (N2),
        Poor Rapport (N3),
        Passive withdrawal (N4), and
        Lack of Spontaneity (N6),
    with moderate or higher severity,
    wherein said moderate or higher severity corresponds to a score equal to 4 or higher before beginning of said treatment, and
    administering to the subject a therapeutically effective amount of a selective D3 antagonist to relieve, alleviate, reverse, or improve at least one symptom of schizophrenia in the subject,
    wherein said selective D3 antagonist is N-(3-{4-[4-(8-oxo-8H-[1,3]dioxolo[4,5-g]chromen-7-yl)-butyl]-piperazin-1-yl}-phenyl)-methanesulfonamide of the following Formula 1 or a pharmaceutically acceptable salt thereof:

Formula 1

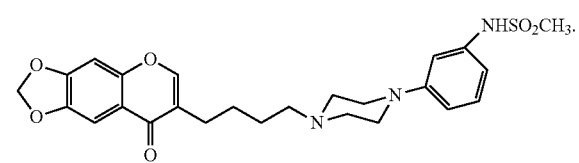

2. The method of claim 1, wherein said pharmaceutically acceptable salt is N-(3-{4-[4-(8-oxo-8H-[1,3]dioxolo[4,5-g] chromen-7-yl)-butyl]-piperazin-1-yl}-phenyl)-methanesulfonamide hydrochloride.

3. The method of claim 1, wherein said subject suffers from acute exacerbation of schizophrenia before beginning of said treatment.

4. The method of claim 3, wherein said acute exacerbation is characterized by a PANSS total score ≥70 and <120.

5. The method of claim 4, wherein said subject meets the following additional criteria:
    a. a well-documented diagnosis of schizophrenia for a minimum of 1 year; and
    b. a Clinical Global Impression of Severity (CGI-S) score≥4,
before beginning of said treatment.

6. The method of claim 1, wherein said therapeutically effective amount is a dose of 1 to 100 mg once daily or 0.5 to 50 mg twice daily.

7. The method of claim 6, wherein said therapeutically effective amount is a fixed dose of 40 mg once daily or 20 mg twice daily.

8. The method of claim 6, wherein said dose is administered orally.

9. The method of claim 6, wherein said dose is administered for 6 weeks or more to the subject in need thereof.

* * * * *